United States Patent [19]

Cheng

[11] Patent Number: 5,336,159
[45] Date of Patent: Aug. 9, 1994

[54] INFRARED MASSAGER

[76] Inventor: Tzu-Keng Cheng, 197 Shin-Sheng Street, Chung-Ho City, Taipei, Taiwan

[21] Appl. No.: 934,325

[22] Filed: Aug. 25, 1992

[51] Int. Cl.⁵ .............................................. A61H 1/00
[52] U.S. Cl. ........................................ 601/15; 601/72; 601/73
[58] Field of Search ................... 128/24 R, 24.1, 24.2, 128/32, 34–36, 41, 59–62 R

[56] References Cited

U.S. PATENT DOCUMENTS

| | | | |
|---|---|---|---|
| 1,710,643 | 4/1929 | Hassler | 128/59 |
| 2,276,510 | 3/1942 | Newton | 128/41 |
| 3,103,925 | 9/1963 | Vogt | 128/59 X |
| 3,467,080 | 9/1969 | McNair | 128/41 X |
| 3,710,785 | 1/1973 | Hilger | 128/36 |
| 3,812,848 | 5/1974 | Kollitz | 128/36 |
| 4,210,134 | 7/1980 | Okazaki et al. | 128/60 X |
| 4,502,469 | 3/1985 | Jaw | 128/24.1 |
| 5,065,743 | 11/1991 | Sutherland | 128/24.1 |
| 5,103,809 | 4/1992 | De Luca et al. | 128/60 |
| 5,105,802 | 4/1992 | Pokorny | 128/61 X |
| 5,176,130 | 1/1993 | Kim | 128/36 |
| 5,187,827 | 2/1993 | Wei | 128/62 R X |

FOREIGN PATENT DOCUMENTS

| | | | |
|---|---|---|---|
| 385711 | 5/1932 | United Kingdom | 128/60 |
| 9104002 | 4/1991 | World Int. Prop. O. | 128/32 |

*Primary Examiner*—Robert A. Hafer
*Assistant Examiner*—Brian E. Hanlon
*Attorney, Agent, or Firm*—Bacon & Thomas

[57] ABSTRACT

An infrared massager includes two massaging devices respectively locked in two receiving chambers on a casing by lock hoods, which include each a plurality of silicon rubber massage elements on a vibrating plate reciprocated by a motor through a cam. Two infrared devices are respectively received in the receiving chambers and are attached to the vibrating plate of each massaging device. The infrared devices include a plurality of infrared light emitting elements controlled to emit infrared light through the silicon rubber massage elements for heating the muscles as the muscles are massaged by the massaging devices.

1 Claim, 3 Drawing Sheets

INFRARED MASSAGER

BACKGROUND OF THE INVENTION

The present invention relates to massagers and relates more particularly to an infrared massager which uses infrared devices to produce heat for stimulating the muscles as the muscles are massaged by motor-operated massaging devices.

A wide variety of massaging devices are known and widely in use for rubbing and kneading the muscles and joints in order to make them work better. These massaging devices are commonly comprised of a plurality of massage elements reciprocated by a motor-driven mechanism. Because these massage elements are simply driven to repeat the same reciprocating movement, less massage effect can be achieved.

SUMMARY OF THE INVENTION

The present invention has been accomplished under the aforesaid circumstances. It is therefore an object of the present invention to provide an infrared massager which produces infrared radiant heat for stimulating the muscles and joints as they are massaged by the rubber massage elements thereof. It is another object of the present invention to provide an infrared massager which comprises a plurality of massaging devices that can be operated separately as well as simultaneously. It is still another object of the present invention to provide an infrared massager which uses rubber bolts to connect the massaging devices to the casing thereof so that the massaging devices can be vibrated for rubbing and kneading the muscles and joints effectively.

DETAILED DESCRIPTION OF THE PREFERRED EMBODIMENT

Figure 1:
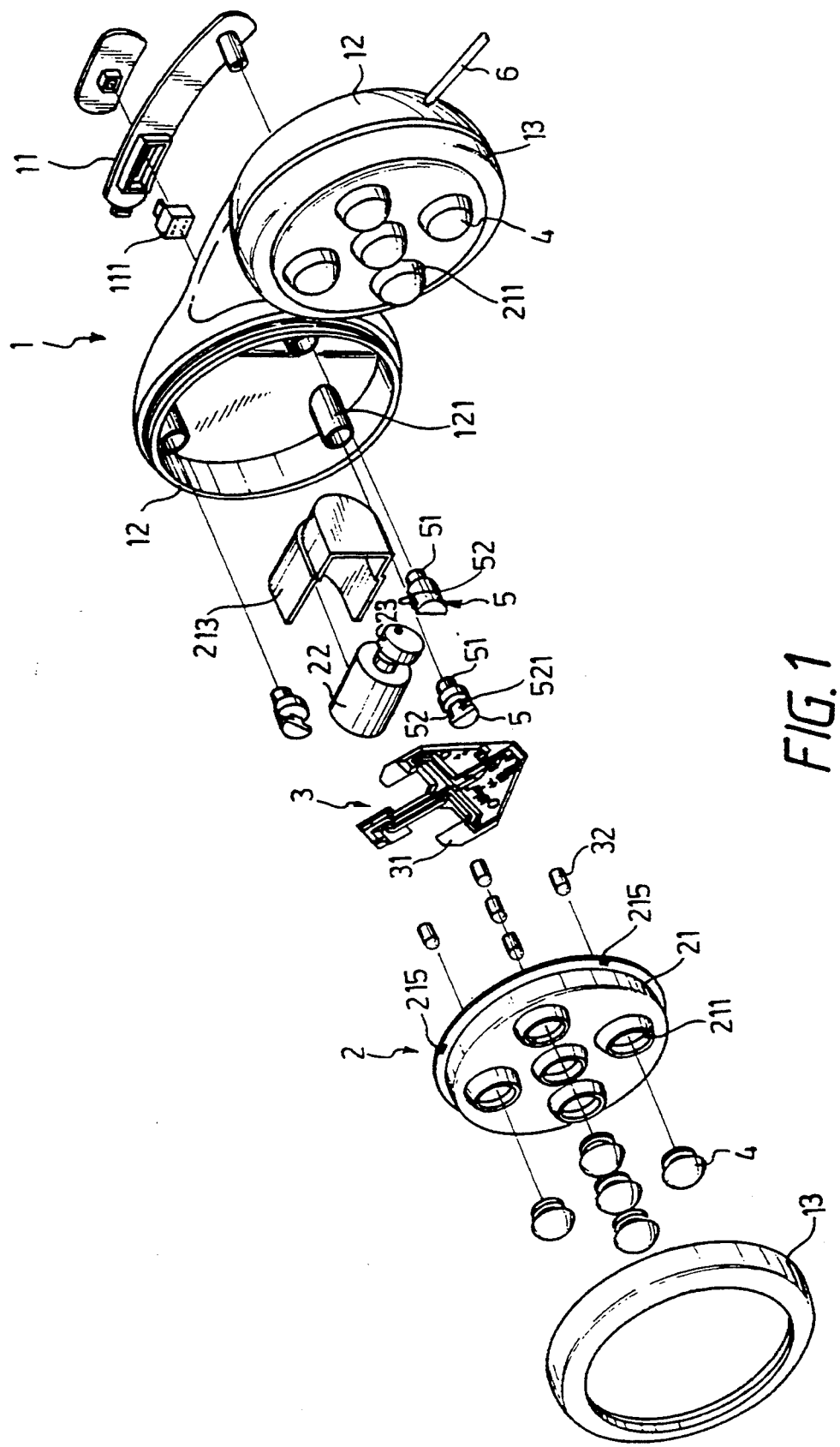
FIG. 1 is an exploded view of the preferred embodiment of the infrared massager of the present invention.
Figure 2:
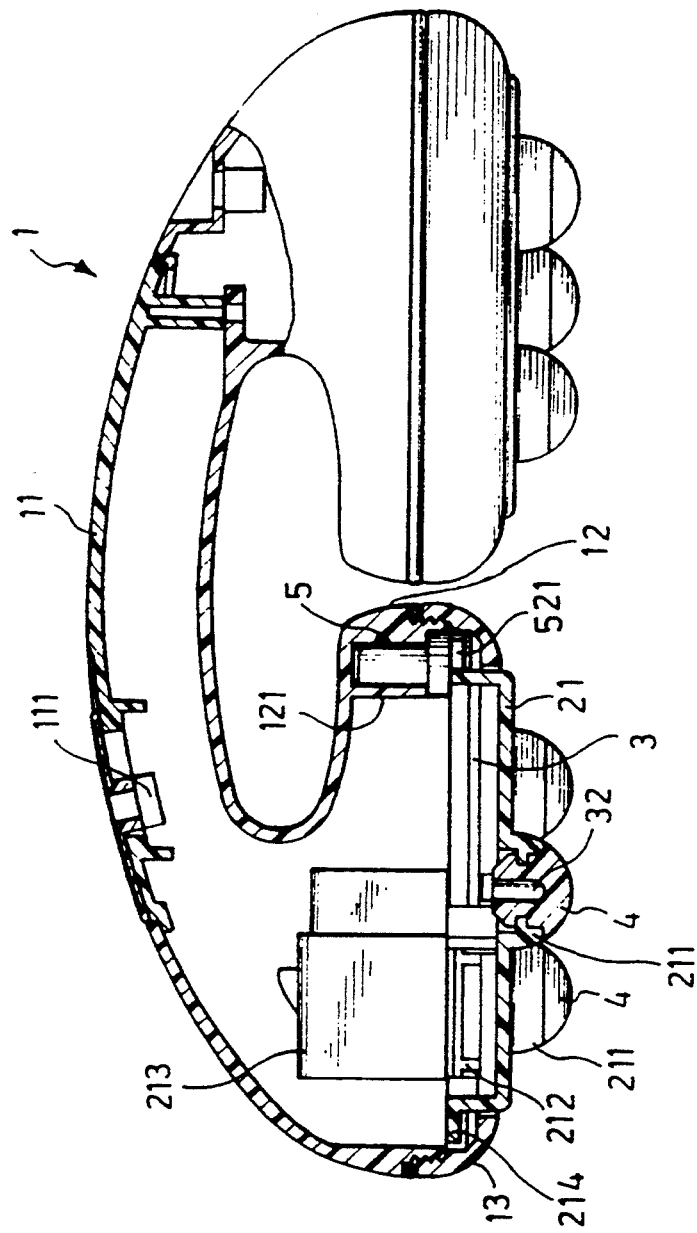
FIG. 2 is a sectional assembly view thereof.

Referring to FIGS. 1 and 2, an infrared massager as constructed in accordance with the present invention is generally comprised of a casing 1 having two receiving chambers 12 on one side and a control handle 11 on an opposite side. The receiving chambers 12 each receive a massaging device 2 and an infrared device 3. A lock hoop 13 is fastened to each of the receiving chambers 12 to lock the respective massaging device and the respective infrared device 3 in place. Each massaging device 2 consists of a vibrating plate 21, a motor 22 and a cam 23. The cam 23 is coupled to the output shaft of the motor 22. Each infrared device 3 is comprised of a plurality of infrared light emitting elements 32 mounted on and controlled by a circuit board 31. The circuit board 31 of each infrared device 3 is fastened to the vibrating plate 21 on the back of each respective massaging device 2 with the infrared light emitting elements 32 inserted into respective holes 211 on the vibrating plate 21 and covered by respective silicon rubber elements 4. When the circuit board 31 is fastened to the vibrating plate 21, the infrared device 3 is secured in place. The vibrating plate 21 of each massaging device 2 has a motor chamber 212 on the back covered with a motor case 213 to hold the motor 22. Rotating the motor 22 causes the cam 23 to vibrate the vibrating plate 21. The vibrating plate 21 is fastened to the casing 1 by a plurality of rubber bolts 5. The rubber bolts 5 are each comprised of a retainer head 52 and a bottom rod 51. The retainer head 52 of each rubber bolt 5 has a projection 521 at its middle. By inserting the bottom rod 51 into a respective stub tube 121 on either receiving chamber 12 on the casing 1 and the projection 521 in a respective notch 215 on a peripheral flange 214 of the vibrating plate 21, the vibrating plate 21 is captured in the respective receiving chamber 12. After the vibrating plate 21 has been captured in the respective receiving chamber 12, the lock hood 13 is covered on the respective receiving chamber 12 to lock the vibrating plate 21 in place.

Figure 3:
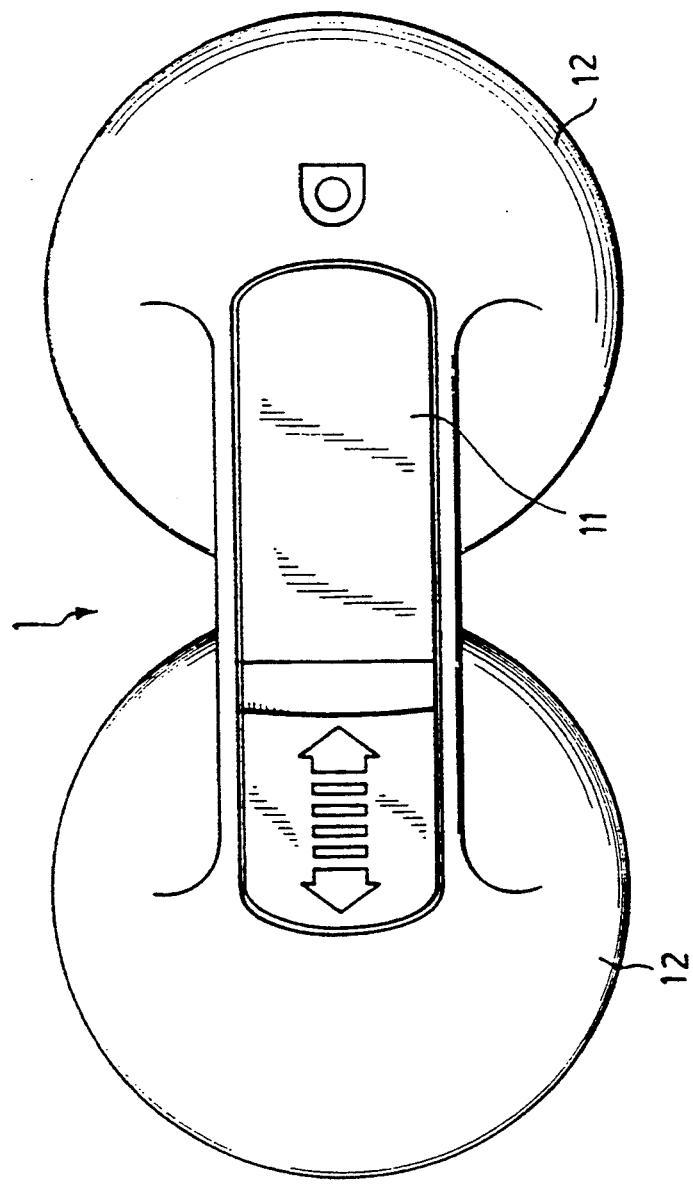
FIG. 3 illustrates the outer appearance of the infrared massager.

Referring to FIG. 3 and seeing FIG. 1 again, the control handle 11 has a control switch 111 for controlling the operation of the two massaging devices 2 and the two infrared device 3. The circuit board 31 of each infrared device 3 and the motor 22 of each massaging device 2 are respectively connected to an external power supply through a cable 6 via the control switch 111. By means of the control of the control switch 111, the two massaging devices 2 may be simultaneously turned on or separately triggered to vibrate the respective vibrating plate 21. When the massaging devices are separately operated, the infrared device or devices are simultaneously turned on to produce infrared radiant heat through the infrared light emitting elements 32. The infrared radiant heat is transmitted through the silicon rubber elements 4 for stimulating the muscles and joints as the silicon rubber elements 4 are vibrated to rub and knead the muscles and joints.

What is claimed is:

1. An infrared massager comprising:
   a) a casing including two receiving chambers, each receiving chamber having a plurality of stub tubes disposed therein;
   b) a massaging device disposed within each receiving chamber, each massaging device including a motor, a cam rotated by the motor, a vibrating plate vibrated by the cam, the vibrating plate having a plurality of holes formed therein and a peripheral flange having a plurality of notches formed therein, and a plurality of silicon rubber massage elements engaged within the holes;
   c) a plurality of rubber bolts, each rubber bolt including a retainer head, a projection and a bottom rod, and the projections of the rubber bolts being engaged within the notches of each peripheral flange for capturing the vibrating plate in the receiving chamber;
   d) a lock hood mounted on each receiving chamber for locking the massaging device inside the chamber;
   e) an infrared device disposed within each receiving chamber and secured to the vibrating plate, each infrared device including a plurality of infrared light emitting elements disposed within the holes of the vibrating plate; and
   f) a control handle for moving the casing, the control handle including a switch for connecting an electric power supply source to each massaging device and infrared device to cause vibration of the vibrating plate and emitting of infrared light by the infrared device for providing heated massage through the rubber massage elements.

* * * * *